United States Patent
Bignozzi et al.

(10) Patent No.: US 8,178,122 B2
(45) Date of Patent: May 15, 2012

(54) USE OF NANOMATERIALS BASED ON TITANIUM DIOXIDE AND ZIRCONIUM DIOZIDE AS COATINGS FOR OSTEOINTEGRATED BIOMEDICAL PROSTHESES, AND OSTEOINTEGRATED BIOMEDICAL PROSTHESES PREPARED THEREWITH

(75) Inventors: Carlo Alberto Bignozzi, London (GB); Francesco Carinci, London (GB); Stefano Caramori, London (GB); Valeria Dissette, London (GB)

(73) Assignee: NM Tech Nanomaterials and Microdevices Technology Ltd., London (GB)

( * ) Notice: Subject to any disclaimer, the term of this patent is extended or adjusted under 35 U.S.C. 154(b) by 465 days.

(21) Appl. No.: 12/304,069

(22) PCT Filed: Aug. 14, 2006

(86) PCT No.: PCT/IT2006/000450
§ 371 (c)(1),
(2), (4) Date: Feb. 9, 2009

(87) PCT Pub. No.: WO2008/020460
PCT Pub. Date: Feb. 21, 2008

(65) Prior Publication Data
US 2009/0270997 A1    Oct. 29, 2009

(51) Int. Cl.
*A01F 13/00* (2006.01)
*A61F 2/00* (2006.01)
*A01N 25/34* (2006.01)
*A01N 55/02* (2006.01)
*A01N 65/00* (2006.01)
*A01N 31/00* (2006.01)
*A61K 31/28* (2006.01)
*A61K 31/095* (2006.01)

(52) U.S. Cl. ........ 424/422; 424/423; 424/404; 514/492; 514/66; 514/706; 514/495

(58) Field of Classification Search ............. 424/422, 424/423, 404; 514/492, 66, 706, 495
See application file for complete search history.

(56) References Cited

U.S. PATENT DOCUMENTS

| 4,906,466 | A | * | 3/1990 | Edwards et al. ............. 424/421 |
| 7,906,132 | B2 | * | 3/2011 | Ziegler et al. ............... 424/409 |
| 2004/0117007 | A1 | * | 6/2004 | Whitbourne et al. ........ 623/1.42 |
| 2005/0084464 | A1 | * | 4/2005 | McGrath et al. ............... 424/67 |
| 2005/0112376 | A1 | | 5/2005 | Naasani |
| 2005/0249760 | A1 | | 11/2005 | Shin-Ching et al. |
| 2005/0265935 | A1 | | 12/2005 | Hollingsworth et al. |
| 2006/0141015 | A1 | * | 6/2006 | Tessier et al. ................ 424/443 |
| 2008/0269186 | A1 | * | 10/2008 | Bignozzi et al. .............. 514/185 |
| 2010/0086605 | A1 | * | 4/2010 | Bignozzi et al. .............. 424/489 |

FOREIGN PATENT DOCUMENTS

| DE | 103 42 258 A1 | 4/2005 |
| EP | 0 937 398 A1 | 8/1999 |
| WO | WO 02/085385 A2 | 10/2002 |
| WO | WO 2004/026346 A2 | 4/2004 |
| WO | WO 2004/073400 A2 | 9/2004 |
| WO | WO 2005/042040 A1 | 5/2005 |
| WO | WO 2005/042041 A1 | 5/2005 |
| WO | WO 2006015317 A2 * | 2/2006 |
| WO | WO 2006/043168 A2 | 4/2006 |
| WO | WO 2006043166 A2 | 4/2006 |
| WO | WO 2006/049379 A1 | 5/2006 |
| WO | WO 2007/122651 A1 | 11/2007 |

OTHER PUBLICATIONS

T. Pham et al., "Preparation and Characterization of Gold Nanoshells Coated with Self-Assembled Monolayers", Langmuir, vol. 18, 2002, pp. 4915-4920.
M.K. Nazeeruddin et al., "Conversion of Light to Electricity by cis-X$_2$Bis(2,2'-bipyridyl-4,4'-dicarboxylate)ruthenium(II) Charge-Transfer Sensitizers (X-Cl-, Br-, I-, CN-, and SCN-) on Nanocrystalline TiO$_2$ Electrodes," *J. Am. Chem. Soc.*, vol. 115, No. 14, 1993, pp. 6382-6390.
Mattigod et al., "Functionalized TiO$_2$ Nanoparticles for Use for in Situ Anion Mobilization," *Environ. Sci. Technol.*, 2005, 39, 7306-7310.
Polleux et al., "Ligand Functionality as a Versatile Tool to Control the Assembly Behavior of Preformed Titania Nanocrystals," *Chem. Eur. J.*, 2005, 11, 3541-3551.

* cited by examiner

*Primary Examiner* — Johann Richter
*Assistant Examiner* — Abigail Fisher
(74) *Attorney, Agent, or Firm* — Dickstein Shapiro LLP

(57) ABSTRACT

Materials and methods, for preparation of coatings based on titanium dioxide for osteointegrated biomedical prostheses. The coatings may comprise nanomaterials having antibacterial properties. For example, an endo-osseous implant is provided with a coating comprised of nanocrystalline material comprising nanoparticles of formula (I)

$$(L\text{-}Me^{n+})i, \quad (I)$$

where $AO_x$ represents $TiO_2$ or $ZrO_2$; $Me^{n+}$ is a metallic ion having antibacterial activity, with n=1 or 2; L is a bi functional organic molecule which can simultaneously bind to the metal oxide and to the metallic ion $Me^{n+}$, and i is the number of $L\text{-}Me^{n+}$ groups bound to one nanoparticle of $AO_x$.

18 Claims, 1 Drawing Sheet

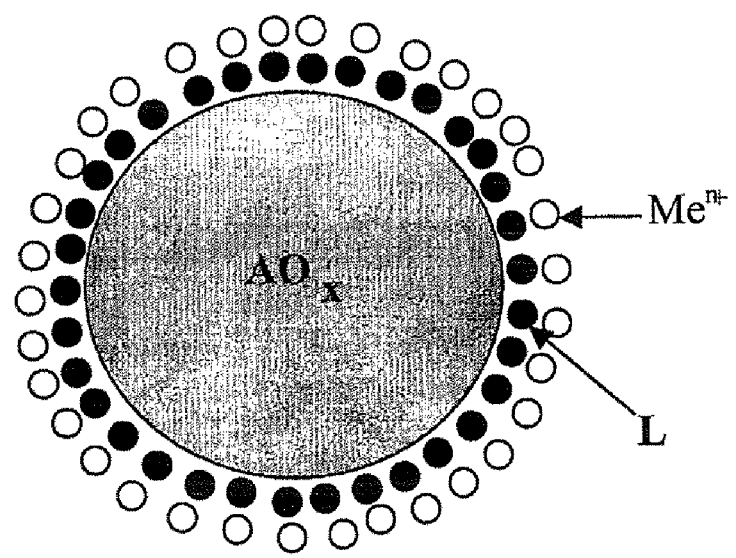

USE OF NANOMATERIALS BASED ON TITANIUM DIOXIDE AND ZIRCONIUM DIOZIDE AS COATINGS FOR OSTEOINTEGRATED BIOMEDICAL PROSTHESES, AND OSTEOINTEGRATED BIOMEDICAL PROSTHESES PREPARED THEREWITH

OBJECT OF THE INVENTION

The present invention relates to materials and methods, for preparation of coatings based on titanium dioxide for osteointegrated biomedical prostheses. Such coatings are realized with nanomaterials having antibacterial properties, and have the purpose of promoting osteointegration of the implants, and, at the same time, reducing rejection attributable to inflammatory processes which derive from infections which may develop in the neighborhood of the implants.

INTRODUCTION

A prosthesis is an apparatus which substitutes for an organ which is missing or has been removed. An organ is an aggregate of diverse tissues which performs a specific function. A tooth is an organ. A dental implant is an example of a prosthesis. Another example is an apparatus used in orthopedics to substitute for the coxofemoral joint.

Such prostheses are comprised of materials (customarily, metals and metal alloys) having specific mechanical properties enabling them to support the attendant high loads. A fundamental property which such a prosthesis inserted into osseous tissue must have is elevated "osteointegration".

Osteointegration is a process by which implanted or grafted material activates the osseous tissue into which it has been implanted or into/onto which it has been grafted, so as to lead to adhesion of the osseous tissue to said material.

The process of osteointegration is very complex and not completely understood. It involves mechanisms of:
   immunogenic surveillance (so-called "recognition of self"), which are typical of all processes which provides for the use of implants;
   osteoconduction (a process by which implanted or grafted material provides a support for growth of new osseous tissue; and
   osteoinduction (a process by which the implanted or grafted material gives rise to one or more molecular signals which induce osteoneogenesis).

The process of osteointegration may be considered to be completed in about 60 days, corresponding to the time for consolidation of fractures.

The effects of the material of which an endo-osseous implant is comprised, and the design of the implant itself, both play major roles in the success of the implant. Both factors influence the osteointegration process, in varying degrees.

Currently, titanium is the material of choice for dental prostheses and for orthopedic prostheses, because it combines excellent mechanical properties and very good osteointegration.

Regarding the designing of implants, ordinarily the following aspects are considered: (1) macro design; (2) mini design; (3) micro design; and (4) nano design. Macro design is the macroscopic design of the implant. With reference to dental implants, for example, there are implants of various shapes, such as cylindrical and conical. Mini design relates, e.g., to the characteristics of the screw threads, and the shapes of the ridges on the threads, which ridges may have blunt edges (rounded edges) or sharp edges, and is on the order of millimeters. The micro design is concerned with the characteristics of the surface, which may be, e.g., smooth or rough. In this connection, there are various methods for determining the differences in the micropores which come to be formed on the surface of an implant. Finally, the nano design is a subject of consideration. The nano design relates to the molecular organization of the surface of the implant. Currently, implants are comprised of titanium, which oxidizes in air to titanium dioxide, with a stochastic distribution of the two crystalline forms rutile and anatase. Preliminary studies available in the literature show that it is possible to produce surfaces completely covered in anatase, which enhances the osteointegrative characteristics of the titanium (Sul, Y. T., Johansson, C. B., Jeong, Y., Roser, K., Wennerberg, A., and Albrektsson, T., 2001, "Oxidized implants and their influence on the bone response," *J. Mater. Sci. Mater. Med.*, 12, 10-12:1025-31; and Giaveresi, G., Ambrosio, I., Battiston, G. A., Casellato, U., Gerbasi, R., Finia, M., Aldini, N. N., Martini, L., Rimondini, L., and Giardino, R., 2004, "Histomorphometric, ultrastructural and microhardness evaluation of the osteointegration of a nanostructured titanium oxide coating by metal-organic chemical vapour deposition: an in vivo study," *Biomaterials*, 25, (November) 25:5583-91).

Zirconium dioxide also has osteoinductive properties (Cabrini, R. L., Guglielmotti, M. B., Almagro, J. C., 1993, "Histomorphometry of initial bone healing around zirconium implants in rats," *Implant. Dent.*, 2:264-7; and Sennerby, L., Dasmah, A., Larsson, B., and Iverhed, M., 2005, "Bone tissue responses to surface-modified zirconia implants: A histomorphometric and removal torque study in the rabbit," *Clin. Implant. Dent. Relat. Res.*, 7, Suppl. 1, S13-20).

Despite the advances described in the areas of materials and the design of osteointegrated implants, a problem which is still unresolved and which manifests particularly in the peri-implant region is that of inflammatory processes of infectious etiology which develop around an implant and which in many cases lead to loss of the implant, resulting in aggravated biological burden as well as increased economic costs. It is apparent that a material which maintained or indeed improved upon the osteointegrative properties of titanium and in addition had high potential anti-infective action would represent a significant advance over currently available osteointegrated biomedical prosthetic devices.

It was recently demonstrated that under conditions of irradiation with photons in the ultraviolet spectral range, anatase has antibacterial properties (Del Curto, B., Brunella, M. F., Giordano, C., Pedeferri, M. P., Valtulina, V., Visai, L., and Cigada, A., 2005, "Decreased bacterial adhesion to surface-treated titanium," *Int. J. Artif. Organs*, 28, (7, July):718-30; and Suketa, N., Sawase, T., Kitaura, H., Naito, M, Baba, K., Nakayama, K., Wennerberg, A., and Atsuta, M., 2005, "An antibacterial surface on dental implants, based on the photocatalytic bactericidal effect," *Clin. Implant. Dent. Relat. Res.*, 7, 2:105-11) However, the need for luminous radiation renders such phenomena unusable for prosthetic applications, particularly endo-osseous implants, where it is clearly not possible to achieve the required illumination of the prosthesis.

SUMMARY OF THE INVENTION

The invention consists of preparation of coatings on endo-osseous implants which implants are comprised of titanium or another metallic material, which coatings are principally comprised of functionalized nanomaterials which are based on titanium dioxide in the anatase allotropic form, or are based on zirconium dioxide, and which comprise silver(I) ions, zinc(II) ions, and/or copper(II) ions. Such coatings display bactericidal and virucidal activity even in the absence of luminous irradiation, and may be used to enhance osteointegration of implants while reducing rejection attributable to inflammation processes of infective etiology.

According to one feature of the present invention, transparent nanocrystalline substrates are applied to endo-osseous implants, which nanocrystalline substrates are based on titanium dioxide or zirconium dioxide, functionalized with derivatives of silver(I), zinc(II), and/or copper(II), and prepared according to procedures described hereinbelow.

The inventive nanocrystalline substrates based on titanium dioxide or zirconium dioxide are essentially nanomaterials which are functionalized with ligands L comprised of organic molecules capable of simultaneously binding to the nanocrystalline substrate and to the metallic ions which display bactericidal am virucidal activity (e.g. monovalent silver ions, $Ag^+$, divalent zinc ions, $Zn^{++}$, or divalent copper ions, $Cu^{++}$). Such ligands L may be referred to as "bifunctional ligands", because they contain groups which can bind to the surface of the nanomaterial and other groups which can link metal ions with bactericidal activity.

According to another feature of the present invention, primers may be prepared which enhance adhesion of functionalized nanocrystalline films based on titanium dioxide or zirconium dioxide to endo-osseous implants comprised, of titanium or another suitable metallic material. The materials and methods of preparation of these coatings are described hereinbelow.

According to yet another feature of the present invention, the functionalized nanocrystalline materials utilized for the purposes of the present invention may be mixed with cationic surfactants having antibacterial activity, which surfactants are capable of adsorbing onto the surface of the nanoparticles of formula $AO_x$ or said surfactants are capable of giving rise to suspensions of the nanomaterials, wherewith the mixtures are stable over time.

BRIEF DESCRIPTION OF THE DRAWINGS

FIG. 1 is a schematic illustration of the structure of an inventive nanoparticle.

DETAILED DESCRIPTION OF THE INVENTION

The nanocrystalline materials functionalized with organic ligands, which materials are used to achieve the purposes of the present invention, are those described in the international patent application PCT/IT2006/000280, of Apr. 24, 2006. Said materials are represented by formula (I):

$$AO_x\text{-}(L\text{-}Me^{n+})_i, \quad (I)$$

where $AO_x$ represents $TiO_2$ or $ZrO_2$;

$Me^{n+}$ is a metallic ion having antibacterial activity, with n=1 or 2 (preferably $Me^{n+}$ is $Ag^+$ or $Cu^{++}$;

L is a bifunctional organic molecule which can simultaneously bind to the metal oxide and to the metallic ion $Me^{n+}$; and i is the number of $L\text{-}Me^{n+}$ groups bound to one nanoparticle of $AO_x$.

The value of the index i depends on various factors, such as: the size(s) of the nanoparticle(s) of $AO_x$, the nature of the ligand L, and the method used for preparation of the ligand L. In the context of the present invention, i corresponds to the number of ligands L to which a nanoparticle of $AO_x$ can bind when said nanoparticle is contacted with a solution of the ligand L for a period between 10 minutes and 72 hours, preferably between 3 and 24 hours.

The inventive nanomaterials have particle sizes less than 40 nm (nanometers), preferably less than 30 nm, particularly preferably less than 15 nm. Nanoparticles of particle size less than 15 nm generally give rise to transparent suspensions, thereby permitting a wider range of applications.

The Bifunctional Ligands L Based on Compounds of an Organic Nature:

The bifunctional ligands L of an organic type which are used according to the present invention include molecular species containing groups which can give rise to an interaction with nanoparticles of $AO_x$, and said molecular species further containing other functionalities which can bind to ions having antibacterial activity. Examples of such molecular species include organic molecules containing the following functional groups:

the carboxylic acid group (carboxy group) (—COOH), the phosphonic acid group (phosphonyl group) (—$PO_3H_2$), and the boronic acid group (boronyl group) (—$B(OH)_2$), which groups are capable of promoting (contributing to) adsorption onto the surface of the oxide $AO_x$; and the groups >N, —$NH_2$, —CN, —NCS, and —SH, which groups are capable of binding to metallic ions having antibacterial activity (such as the ions $Ag^+$, $Zn^{2+}$ and $Cu^{2+}$).

These organic ligands [L] are preferably chosen from among:

nitrogen-containing heterocyclic rings having 6-18 members (preferably chosen from among pyridine, dipyridyl, and terpyridyl), substituted with one or more substituents chosen from among: the carboxylic acid group (carboxy group) (—COOH), the boronic acid group (boronyl group) (—$B(OH)_2$), the phosphonic acid group (phosphonyl group) (—$PO_3H_2$), the mercapto group (—SH), and the hydroxyl group (—OH);

C6-C18 aryl compounds (preferably chosen from among phenyl, naphthyl and biphenyl), substituted with one or more substituents chosen from among: the carboxylic acid group (carboxy group) (—COOH), the boronic acid group (boronyl group) (—$B(OH)_2$), the phosphonic acid group (phosphonyl group) (—$PO_3H_2$), the mercapto group (—SH), and the hydroxyl group (—OH);

C2-C18 monocarboxylic acids and dicarboxylic acids, substituted with one or more mercapto groups (—SH) and/or hydroxyl groups (—OH).

More preferable examples of such bifunctional ligands [L] of an organic type include:

pyridine, dipyridyl, and terpyridyl, functionalized with: carboxylic acid group(s), boronic acid group(s), or phosphonic acid group(s);

mercaptosuccinic acid, mercaptoundecanoic acid, mercaptophenol, mercaptonicotinic acid, 5-carboxypentanethiol, mercaptobutyric acid, and 4-mercaptophenyl-boronic acid.

The distinctive nature of these substrates is connected to the homogeneous distribution of the silver(I), zinc(II), and/or copper(II) ions on the nanoparticles of titanium dioxide or zirconium dioxide, as illustrated schematically in FIG. 1.

The preparation of such nanocrystalline materials, and the coating of endo-osseous implants with such materials, are described hereinbelow.

(A) Preparation of Transparent Suspensions Based on $TiO_2$:

Into a beaker there were placed 300 mL distilled $H_2O$ and 2.1 mL of a strong acid, e.g. concentrated $HNO_3$ (65 wt. %).

Over a period of 10 min, under agitation, with the aid of a dropping funnel, 50 mL titanium isopropoxide (supplied by Fluka) was added. Immediately, a white milky precipitate comprised of $TiO_2$ was formed. The mixture was then heated to 80° C. for 8-12 hours, taking care to maintain the agitation and the temperature constant. During the heating, the precipitate redissolved and the mixture acquired an opalescent appearance. During the heating period, the colloidal suspension was allowed to concentrate to a final volume of 100 to 200 mL, corresponding to a $TiO_2$ concentration of 150 g/L to 75 g/L. The nanoparticles of titanium dioxide obtained at the end of the process had a diameter which varied in the range of 6-15 nm. The suspension which had been concentrated to 100 mL was then diluted by addition of 400 mL distilled water and 500 mL absolute ethanol, giving rise to a final solution which was transparent, had pH about 2, and contained $TiO_2$ in a concentration of 1.5%, in the volume of 1 L.

(B) Preparation of Transparent Suspensions Based on $ZrO_2$:

Into a beaker there were placed 300 mL distilled $H_2O$ and 2.1 mL of a strong acid, e.g. concentrated $HNO_3$ (65 wt. %). Over a period of c. 10 min, under agitation, with the aid of a dropping funnel, 76 mL of a 70% solution of zirconium tetraisopropoxide in isopropanol was added.

It was noted that a white milky precipitate comprised of $ZrO_2$ was immediately formed. The mixture was then heated to 90° C. for 8-12 hours, taking care to continue the agitation and to maintain the temperature constant. During the heating, the precipitate redissolved, giving rise to a suspension having a milky appearance, which suspension was allowed to concentrate to a volume of 140 to 280 mL, corresponding to a $ZrO_2$ concentration of 150 g/L to 75 g/L. The suspension which had been concentrated to 140 mL was then diluted by addition of 560 mL distilled water and 700 mL absolute ethanol, to obtain 1.4 L of an opalescent suspension which had pH about 2 and which contained $ZrO_2$ in a concentration of 1.5%

(C) Preparation of Neutral Transparent Suspensions of Titanium Dioxide:

Neutral aqueous suspensions based on titanium dioxide, which suspensions have an opalescent appearance, can be prepared from peroxytitanic acid as a starting material.

A typical such preparation is as follows: 150 mL of $TiCl_4$ in 20% HCl is placed in a beaker of volume 1 L, and 826 mL $NH_4OH$ diluted 1:9 with distilled water is added to this solution. The pH of the resulting solution is neutral (pH=7), and one obtains a precipitate of titanic acid $Ti(OH)_4$ of a white color and having a gel consistency. The precipitate is collected on a filter of porosity G3 and is washed with 750-1000 mL distilled water so as to completely remove chloride (verifiable by treating the filtrate liquid with $AgNO_3$). (If chloride is present, a white caseous precipitate of AgCl will be noted.) The precipitate comprising titanic acid, $Ti(OH)_4$, is collected and is suspended in 200 mL distilled water having conductivity less than 1.5 µS (microsiemens) and pH in the range 5-7, and 92 mL 30% $H_2O_2$ is added slowly over a period of 20-30 min. The dissolution of the precipitate is noted, along with the formation of a yellow-colored solution containing peroxytitanic acid of general formula

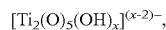

where x may vary in the range 3 to 6.

The solution is then heated 1 hr at 70° C., in order to decompose the excess $H_2O_2$, and is then placed in an autoclave for 8 hr at 120° C. During this period the peroxytitanic acid decomposes to titanium dioxide which is prevalently in the allotropic form of anatase. The resulting suspension of nanoparticles has a pH close to neutral, with an opalescent appearance, and is stable over time.

Production of Suspensions of Nanomaterials Having Antibacterial and Antiviral Activity:

In order to obtain films having bactericidal and antiviral activity, the suspensions of nanomaterials described in sections (A), (B), and (C) can be functionalized with silver ions. The method of preparation employs:

a first stage of adsorption onto the nanoparticles comprised of titanium dioxide or zirconium dioxide, with a bifunctional ligand L; followed by mixture with an aqueous or organic solution containing $Ag^+$ ions.

It is also possible to bring about adsorption, onto the nanoparticles, of an alkylammonium salt which is a cationic surfactant having bactericidal activity, by mixing with the suspension of nanomaterials functionalized with $Ag^+$ ions.

In general, the adsorption of the bifunctional ligand L on the nanomaterials described in the present invention requires about 12-24 hours, whereas the binding of the $Ag^+$ ions to the ligand L is stabilized instantaneously when solutions containing these ions are added to the suspensions of the nanomaterials functionalized with the ligand L.

The preparation methods described hereinbelow describe in details the preparative methodologies for functionalization of the suspensions of the nanomaterials with:

the bifunctional ligands L;
$Ag^+$ ions; and
cationic surfactants.

Analogous preparation methods may be employed in which the suspensions are functionalized with $Cu^{2+}$ ions.

(D) Adsorption of 4-mercaptophenylboronic acid and $Ag^+$ Ions onto Transparent Suspensions of $TiO_2$ Prepared According to Method (A), and onto Products Supplied by the Firm Eco Coating Photocatyst S.r.l.:

100 mL of a transparent suspension of titanium dioxide prepared according to method (A) and containing 15% $TiO_2$ was diluted with 600 mL distilled water and 300 mL ethanol. To the resulting suspension, 0.052 g 4-mercaptophenylboronic acid was added. The suspension was maintained under agitation 24 hr, at the end of which it was revealed spectrophotometrically that the boronic acid had been completely adsorbed onto the nanoparticles of the semiconductor. To the transparent and odorless suspension there was added, under agitation, a stoichiometric quantity (with respect to the ligand L) of a silver salt such as, e.g., silver lactate or silver acetate (0.06 g in the case of silver lactate).

Benzalkonium chloride was added to the final suspension in an amount to make 0.6 wt. %. The transparent suspension was indefinitely stable; hereinbelow it will be designated as "Bactercline". The same procedure can be utilized to modify transparent suspensions of nanomaterials supplied commercially under the letter designation "PSO 419" by the firm Eco Coating S.r.l.; the amount of the bifunctional ligand and silver ions used in those cases will be based on the content of titanium dioxide in the product. E.g., the product "PSO 419 D2", which is analogous to the product prepared according to method (A), contains 2% $TiO_2$, and has pH about 2, can be converted into an antibacterial and antiviral product by the following method:

50 mL of a PSO 419 D2 solution containing 2% $TiO_2$ is diluted with 50 mL ethanol. To the resulting suspension, 2.2 mg 4-mercaptophenylboronic acid ($2.05 \times 10^{-5}$ M) is added, and the suspension is agitated for 24 hr. At the end of this period, the resulting solution is odorless; 2.8 mg silver lactate is added. The resulting transparent suspension is indefinitely stable.

(E) Use and Preparation of Primers:

According to another feature of the present invention, the inventive endo-osseous implants are coated with primers capable of promoting the adhesion of said nanoparticles having bactericidal, virucidal, and fungicidal activity (according to formula (I) supra) to the titanium implant. Such primers may be of various types, e.g. they may comprise inorganic nanocrystalline products based on titanium dioxide provided commercially by the firm Eco Coating Photocatalyst S.r.l. under the product names "AT-01", "ATLS-01G", and "PSO 419", or they may comprise organic products such as, e.g., styrene-maleic anhydride copolymers or styrene-acrylate copolymers. Preferably, the primers are based on peroxytitanic acid.

The method of preparation of a solution of such a primer is described hereinbelow.

A typical preparation method is as follows: 150 mL TiCl$_4$ in 20% HCl is placed in a beaker of volume 1 L, and 826 mL NH$_4$OH diluted 1:9 with distilled water is added to this solution. The pH of the resulting solution is neutral (pH=7), and one obtains a precipitate of titanic acid Ti(OH)$_4$ of a white color and having a gel consistency. The precipitate is collected on a filter of porosity G3 and is washed with 750-1000 mL distilled water so as to completely remove chloride (verifiable by treating the filtrate liquid with AgNO$_3$). (If chloride is present, a white caseous precipitate of AgCl will be noted.) The precipitate comprising titanic acid, Ti(OH)$_4$, is collected and is suspended in 200 mL distilled water having conductivity less than 1.5 µS and pH in the range 5-7, and 92 mL 30% H$_2$O$_2$ is added slowly over a period of 20-30 min The dissolution of the precipitate is noted, along with the formation of a yellow-colored solution containing peroxytitanic acid of general formula

where x may vary in the range 3 to 6 (wherewith accordingly it is not possible to specify the coordination number of the hydroxyl group (—OH)).

The solution is then heated 1 hr at 70° C., in order to decompose the excess H$_2$O$_2$.

Preparation of Coatings Comprised of Nanomaterials Having Bactericidal and Virucidal Activity, Applied to Endo-Osseous Implants:

The suspensions of nanomaterials described in Sections (A), (B), and (C) can be applied to endo-osseous implants comprised of titanium or other materials, the application being by dip coating or spray coating, followed by drying at ambient temperature, and successive heating to a temperature in the range 50-600° C., preferably 200-500° C., in the presence of oxygen. The preventive application of the primer described in Section (E) facilitates adhesion of the films comprised of the products of (A), (B), and (C). Implants thus treated have antibacterial characteristics in the presence of luminous irradiation in the near ultraviolet range of c. 360-400 nm. Subsequent treatment with the suspensions described in Section (D), which suspensions also can be applied to the implants by dip coating or spray coating, and stabilized by heating at a temperature in the range 80-160° C., confers bactericidal and virucidal properties to the implants even in the absence of luminous irradiation.

According to, a preferred embodiment of the invention, the nanocrystalline materials of formula (I) used for the purposes of the invention comprise cationic surfactants with antibacterial activity capable of promoting adsorption to the surfaces of the nanoparticles of AO$_x$, or capable of giving rise, in mixtures with the suspensions of nanomaterials, to mixtures which are stable over time.

The nanocrystalline materials thus obtained can be caused to adsorb onto the surface of an endo-osseous implant, with or without prior application of a primer, according to the methods described hereinabove.

The preparation of nanocrystalline materials of formula (I) with adsorbed cationic surfactants will be described hereinbelow.

(F) Adsorption of Cationic Surfactants onto Titanium Dioxide:

Cationic surfactants with antibacterial activity can in principle be adsorbed onto nanomaterials based on TiO$_2$, ZrO$_2$, SnO$_2$, ZnO and SiO$_2$. The adsorption results nearly instantaneously in negatively charged or neutral particles. In the case of suspensions of nanomaterials with basic pH, the addition of benzalkonium salts, e.g., benzyl dodecyl dimethylammonium chloride, or benzyl hexadecyl dimethylammonium chloride, or benzalkonium chloride, causes precipitation of the suspension, whereas in the case of suspensions of nanomaterials with neutral or acid pH, the suspension is stable.

The adsorption of benzalkonium chloride on TiO$_2$-based nanomaterials under conditions of neutral pH is demonstrated indirectly from conductimetric measurements. In theory, the adsorption of the dialkylammonium cations onto the TiO$_2$ should result in reduced conductivity; this was verified by the following experiment:

A 50% (wt./vol.) solution of benzalkonium chloride diluted 1:10 (vol./vol.) has conductivity 4.7 mS. If 10 mL of this solution is brought to a volume of 15 mL by addition of distilled water, the conductivity decreases to 3.90 mS; correspondingly, if the 10 mL is brought to 15 mL (diluted to 15 mL) by addition of 5 mL of the neutral suspension of titanium dioxide prepared according to method (C) (said preparation starting with peroxytitanic acid), or using the equivalent product with neutral pH which product is designated "TAT-03", the resulting conductivity measured is 3.60 mS. The 300 µS reduction in the conductivity may be attributed to adsorption of the cationic surfactant onto the surface of the titanium dioxide.

Bactericidal and Virucidal Activity of the Suspensions of Titanium Dioxide Described in Section (D):

The suspensions described in Section (D), which suspensions are based on titanium dioxide functionalized with the ligand 4-mercaptophenylboronic acid and silver ions, display bactericidal and virucidal activity even in the absence of luminous irradiation. The experiments described hereinbelow, relating to "Bactercline" material, are evidence of the activity of the product; wherewith said product when applied as a final coating to the endo-osseous implants will confer upon them its bactericidal and virucidal characteristics.

Evaluation of Bactericidal Activity in Suspensions: Method with Dilution and Neutralization (Standard Method UNI-EN 1276, April 2000): Microorganisms:

The following test strains were used:

*Pseudomonas aeruginosa*
*Staphylococcus aureus*
*Staphylococcus epidermidis*
*Enterococcus faecalis*
*Escherichia coli*
*Salmonella*
*Listeria.*

Origin of the Microorganisms:

All of the bacterial strains used in the tests were obtained from the Department of Experimental Medicine and Diagnostics, Microbiology Section, University of Ferrara. The test product was diluted to 80%.

A test substance was considered to be bactericidal if for each of the bacterial strains, at 20° C., after a contact time of 5 min, the substance caused a reduction in vitality by a factor of at least $10^5$.

The results obtained indicate that in all instances a reduction in vitality by a factor greater than $10^5$ was observed.

Conclusions:

Based on the results obtained, taking into account the validity criteria used for the test, the substance tested was found to be bactericidal against; Pseudomonas aeruginosa, Escherichia coli, Enterococcus faecalis, Staphylococcus epidermidis, Staphylococcus aureus, Salmonella, and Listeria, at a concentration of 80% (which turned out to be the maximum testable concentration), after 5 min of contact, in the presence of bovine albumin at a final concentration of 0.3%, in accordance with UNI-EN 1276, April 2000.

Evaluation of Bactericidal Activity in a Surface Test (UNI-EN 13697, December 2001):

Microorganisms:

In addition to the strains used previously for the test in suspension, in this case the experimentation was extended to:

Legionella pneumophila.

The complete list of the strains tested in the surface test is the following:

Pseudomonas aeruginosa
Staphylococcus aureus
Staphylococcus epidermidis
Enterococcus faecalis
Escherichia Coli
Salmonella
Listeria
Legionella pneumophila.

A test substance was considered to be bactericidal against the microbial strains under the conditions of the European Standard if for each of the bacterial strains, at 20° C., after a contact time of 5 min, the substance caused a reduction in vitality by a factor of at least $10^4$.

The results obtained, reported in the following Table, indicate that in all cases the decimal logarithm of the antimicrobial activity is greater than 4.

| Test microorganisms: | Contact time: 5 min. [Concentration of test substance on surface:] 100% Log (base 10) of the antimicrobial activity: |
|---|---|
| Staphylococcus aureus | >4.02 |
| Staphylococcus epidermidis | >4.00 |
| Pseudomonas aeruginosa | >4.00 |
| Escherichia coli | >4.00 |
| Enterococcus faecalis | >4.19 |
| Salmonella | >4.00 |
| Listeria | >4.00 |
| Legionella pneumophila | >4.26 |

Conclusions:

Based on the results obtained, taking into account the validity criteria used for the test, the substance tested under the experimental conditions adopted was found to be bactericidal against; Pseudomonas aeruginosa, Escherichia coli, Enterococcus faecalis, Staphylococcus epidermidis, Staphylococcus aureus, Salmonella Listeria, and Legionella pneumophila, at a concentration of 100%, after 5 min of contact, in the presence of bovine albumin at a final concentration of 0.3%, in accordance with UNI-EN 13697, December 2001.

Evaluation of Fungicidal Activity in Suspensions: Method with Dilution and Neutralization (UNI-EN 1650, October 2000):

Microorganisms:

The following test strains were used:

Candida albicans

Aspergillus niger.

The strains were obtained from the Department of Experimental Medicine and Diagnostics, Microbiology Section, University of Ferrara.

A test substance was considered to be fungicidal if for each of the mycotic strains, at 20° C., after a contact time of 15 min, the substance caused a reduction in vitality by a factor of at least $10^4$.

Results:

The values of reduction in vitality for various concentrations of the substance being tested are reported in the following Table:

| | Contact time: 15 minutes. Reduction in vitality (at various concentrations "C") (factor): | | |
|---|---|---|---|
| Test microorganism: | C = 25% | C = 50% | C = 80% |
| Candida albicans | >1.13 × $10^4$ | >1.13 × $10^4$ | >1.13 × $10^4$ |
| Aspergillus niger | <1.87 × $10^3$ | >1.37 × $10^4$ | >1.37 × $10^4$ |

Conclusions:

Based on the results obtained, taking into account the validity criteria used for the test, the substance tested was found to be fungicidal against Candida albicans at concentrations of 25%, 50%, and 80%, and against Aspergillus niger at concentrations of 50% and 80% (80% having turned out to be the maximum testable concentration), after 15 min of contact, in the presence of bovine albumin at a final concentration of 0.3%, in accordance with UNI-EN 1650, October 2000.

Evaluation of Fungicidal Activity in a Surface Test (UNI-EN 13697, December 2001):

Microorganisms:

The following test strains were used:

Candida albicans

Aspergillus niger.

The strains were obtained from the Department of Experimental Medicine and Diagnostics, Microbiology Section, University of Ferrara.

A test substance was considered to be fungicidal if, at 20° C., after a contact time of 15 min, the logarithm of the antimicrobial activity against the strains of microbes was at least 3, under the conditions of the above-mentioned European Standard.

Results:

The logarithms of the reduction of vitality are reported in the following Table:

| Test microorganism: | Contact time: 15 minutes. Reduction in vitality (at various concentrations "C") (log(base 10) of the reduction factor): | |
|---|---|---|
| | C = 50% | C = 100% |
| Candida albicans | 2.02 | >3.18 |
| Aspergillus niger | 1.14 | >3.04 |

Conclusions;

Based on the results obtained, taking into account the validity criteria used for the test, the substance tested was found to be fungicidal against *Candida albicans* and *Aspergillus niger* at a concentration of 100%, after 15 min of contact, in the presence of bovine albumin at a final concentration of 0.3%, in accordance with UNI-EN 13697, December 2001.

Evaluation of Virucidal Activity:

The experiments described hereinbelow demonstrate that the product tested is capable of displaying very high virucidal activity against HSV-1 virus (Herpes simplex virus 1), at very low concentrations.

Experimental Method:

Viral preparates were prepared which contained various amounts of a suspension of the virus in modified Dulbecco medium (D-MEM) containing fetal bovine serum (FBS) in the amount of 1%. The amount of virus used (viral titer) was $1 \times 10^6$ cytolysis plaque forming units (Pfu). Various amounts of the product being tested were added, with pretreatment times of 1 hr and 5 hr. The controls consisted of untreated viral suspensions. After the incubation time at room temperature, all the samples were diluted to known volumes to titer the virus. The viral titers of the controls and of the specimens treated with the substance being tested were determined by the procedure described hereinbelow.

A viral titer is determined by calculating the number of infectious viruses present in 1 mL solution. One method used for this consists of determining the number of cytolysis plaques produced by a sufficiently diluted viral suspension contacted with a monolayer of cells. In the series of experiments conducted in this connection, the cells used were renal cells of *Simia africana* (Vero). The cells were cultured at 37° C. in D-MEM in the presence of 5% of $CO_2$ with addition of FBS in the amount of 10%, L-glutamine in the amount of 1%, and penicillin-streptomycin in the amount of 1%. The determination of the titer was carried out on well plates having 12 wells each. When the cultures were nearly confluent, the viral stock was diluted to the concentrations noted, in a medium containing 2% FBS. For each dilution, 2 wells of a well plate were inoculated. After 1 hr incubation at 37° C., the inoculum was aspirated and the infection was arrested by adding a medium containing 1% FBS and 2% human gamma globulin, which had the function of inhibiting production of secondary plaques.

The infected (inoculated) cultures were incubated at 37° C. for 2 days and were monitored until lysis plaques were visible. At this point the cells were fixed and were stained with gentian violet. The number of plaques present in the wells were counted under an optical microscope, and the number of plaques was multiplied by the dilution factor, to obtain the viral titer in units of Pfu/mL.

Results, and Discussion of Results:

Virucidal Activity of the Product being Tested:

The product being tested, in the amount of 10 or 50 microliter, was contacted with the HSV-1 having a viral titer of $1 \times 10^6$ Pfu. Incubation was carried out in 1 mL D-MEM medium containing 1% of FBS; the incubation times employed were (in the alternative) 1 hr and 5 hr. After the given incubation period, the virus was diluted to (in the alternative) $1 \times 10^3$ Pfu and $1 \times 10^2$ Pfu, and the nearly confluent cultures were inoculated. As illustrated in Table 1, the cells inoculated with the virus pretreated with the product being tested did not develop lysis plaques, for both of the pretreatment times and both of the dilutions of the virus.

TABLE

| Pretreatment of HSV-1 (titer $1 \times 10^6$) with 10 microliter and 50 microliter of the product: Dilution of the HSV-1 to $1 \times 10^3$ Pfu: | | | | | | | | | |
|---|---|---|---|---|---|---|---|---|---|
| Medium controls (Pfu) | | Medium pretreated with 10 µL (Pfu) | | Inhibition of plaque formation (%) | Medium pretreated with 50 µL (Pfu) | | Inhibition of plaque formation (%) | Viral titer of the controls | |
| 1 hr | 5 hr | 1 hr | 5 hr | 1 hr, and 5 hr | 1 hr | 5 hr | 1 hr, and 5 hr | 1 hr | 5 hr |
| 263 | 178 | 0 | 0 | 100 | 0 | 0 | 100 | $2.63 \times 10^5$ | $1.78 \times 10^5$ |

The viral titers of the HSV-1 controls which titers are indicated in the Table were calculated by multiplying the mean number of cytolysis plaques by the dilution factor ($10^3$). As seen from the Table, the treated displayed a 100% reduction in formation of cytolysis plaques in comparison to the controls.

For both of the pretreatment times and both of the dilutions of the virus, there was nearly complete reduction of virus particles present. The product tested reduced the viral titer from c. 300,000 viral particles present in the controls to a viral titer of less than 1000. This means that in 1 hr of contact, at a dilution of 10 microliter per mL (1%), there was nearly complete mortality of the viral particles.

Conclusions:

The study of the antiviral activity of the product demonstrates that the product has antiviral activity under direct contact with HSV-1 virus, even under conditions of extreme dilution, for a contact time of 1 hr.

The experiments conducted reveal that the product is capable of achieving nearly complete mortality of viral particles, at a dilution of the product of about 1:100.

The invention claimed is:

1. An endo-osseous implant comprised of biocompatible metallic materials, characterized in that said implant comprises a coating comprised of nanocrystalline material comprising nanoparticles of formula (I):

$$AO_x\text{-}(L\text{-}Me^{n+})_i, \quad (I)$$ 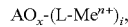

where $AO_x$ represents $TiO_2$ or $ZrO_2$;
$Me^{n+}$ is a metallic ion having antibacterial activity, with n=1 or 2;

L is a bifunctional organic molecule which can simultaneously bind to the metal oxide and to the metallic ion $Me^{n+}$; and i is the number of $L-Me^{n+}$ groups bound to one nanoparticle of $AO_x$, wherein L is 4-mercaptophenylboronic acid wherein $AO_x$ is functionalized with 4-mercapotophenylboronic acid and 4-mercaptophenylboronic acid binds $Me^{n+}$.

2. The endo-osseous implant according to claim 1, wherein the metallic ion having antibacterial activity is selected from the group consisting of $Ag^+$, $Zn^{++}$, and $Cu^{++}$.

3. The endo-osseous implant according to claim wherein the $TiO_2$ is in the allotropic form of anatase.

4. The endo-osseous implant according to claim 1, wherein the coating comprised of nanocrystalline material is transparent.

5. The endo-osseous implant according to claim 1, wherein i represents the number of ligand molecules L with which the nanoparticle of $AO_x$ can bind when said nanoparticle is placed in contact with a solution of the ligand L for a period between 10 minutes and 72 hours.

6. The endo-osseous implant according to claim 1, wherein the nanoparticles have particle sizes less than 40 nm (nanometers).

7. The endo-osseous implant according to claim 1, wherein the nanoparticles have particle sizes less than 30 nm.

8. The endo-osseous implant according to claim 1, wherein the nanocrystalline material is adsorbed onto the surface of said endo-osseous implant.

9. The endo-osseous implant according to claim 1; wherein a primer is interposed between the surface of the endo-osseous implant and the nanoparticles of formula (I), which primer is intended to promote the fixation of said nanoparticles to the surface of the implant.

10. The endo-osseous implant according to claim 9; wherein said primer is based on peroxytitanic acid, or comprises products based on nanocrystalline titanium;

or is based on organic products.

11. The endo-osseous implant according to claim 1, wherein the coating comprised of nanocrystalline material is comprised of cationic surfactants having antibacterial activity.

12. The endo-osseous implant according to claim 11, wherein the cationic surfactants are capable of adsorbing onto the surface of the nanoparticles of formula $AO_x$.

13. The endo-osseous implant according to claim 12, wherein the cationic surfactants are selected from the group consisting of benzyl dodecyl dimethylammonium chloride, benzyl hexadecyl dimethylammonium chloride, and benzalkonium chloride.

14. The endo-osseous implant according to claim 1, wherein the coating comprised of nanocrystalline material is obtained by means of dip coating or spray coating, followed by drying at ambient temperature, and successive heating to a temperature in the range 50-600° C.

15. A method of making a coating on a medical device, comprising a coating having antibacterial properties, antiviral properties, or both antibacterial and antiviral properties on a coating on a medical device, the coating comprising nanoparticles of formula (I):

$$AO_x\text{-}(L\text{-}Me^{n+})_i, \qquad (I)$$

where $AO_x$ represents $TiO_2$ or $ZrO_2$;

$Me^{n+}$ is a metallic ion having antibacterial activity, with n=1 or 2;

L is a bifunctional organic molecule which can simultaneously bind to the metal oxide and to the metallic ion $Me^{n+}$; and i is the number of $L-Me^{n+}$ groups bound to one nanoparticle of $AO_x$;

wherein L is 4-mercaptophenylboronic acid wherein $AO_x$ is functionalized with 4-mercapotophenylboronic acid and 4-mercaptophenylboronic acid binds $Me^{n+}$.

16. A method according to claim 15, wherein the antibacterial, antiviral, or antibacterial and antiviral properties are present in the absence of luminous radiation.

17. The endo-osseous implant according to claim 1, wherein the nanoparticles have particle sizes less than 15 nm.

18. The endo-osseous implant according to claim 1, wherein the coating comprised of nanocrystalline material is obtained by means of dip coating or spray coating, followed by drying at ambient temperature, and successive heating to a temperature in the 200-500° C. in the presence of oxygen.

* * * * *